(12) United States Patent  (10) Patent No.: US 9,101,320 B2
Cummins et al.  (45) Date of Patent: Aug. 11, 2015

(54) SKIN DIAGNOSTIC AND IMAGE PROCESSING METHODS

(71) Applicant: ELC Management LLC, New York, NY (US)

(72) Inventors: Phillip Cummins, Livingston, NJ (US); Garrett W. Vanderover, Bellerose, NY (US); Lise W. Jorgensen, Trumbull, CT (US); David M. Adams, New York, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 13/859,359

(22) Filed: Apr. 9, 2013

(65) Prior Publication Data

US 2014/0323873 A1   Oct. 30, 2014

(51) Int. Cl.
*A61B 5/00* (2006.01)
*G06T 7/00* (2006.01)
*G06K 9/00* (2006.01)

(52) U.S. Cl.
CPC ............... *A61B 5/441* (2013.01); *A61B 5/0077* (2013.01); *G06K 9/00234* (2013.01); *G06T 7/0016* (2013.01); *A61B 5/442* (2013.01); *G06T 2207/30088* (2013.01)

(58) Field of Classification Search
USPC ........................................ 600/407, 473, 476
See application file for complete search history.

(56) References Cited

U.S. PATENT DOCUMENTS

| | | |
|---|---|---|
| 5,478,238 A | 12/1995 | Gourtou et al. |
| 5,537,211 A | 7/1996 | Dial |
| 5,562,109 A | 10/1996 | Tobiason |
| 5,622,692 A | 4/1997 | Rigg et al. |
| 5,636,637 A | 6/1997 | Guiolet et al. |
| 5,785,960 A | 7/1998 | Rigg et al. |
| 5,797,750 A | 8/1998 | Gouriou et al. |

(Continued)

FOREIGN PATENT DOCUMENTS

| | | |
|---|---|---|
| WO | 2010028247 A2 | 3/2010 |
| WO | 2011112422 A2 | 9/2011 |

(Continued)

OTHER PUBLICATIONS

N. Bhatti et al., "Mobile Cosmetics Advisor: An Imaging Based Mobile Service," Multimedia on Mobile Devices, Proceedings of SPIE—IS&T Electronic Imaging, Jan. 2010, 11 pages, vol. 7542.

*Primary Examiner* — Unsu Jung
*Assistant Examiner* — Phong K Huynh
(74) *Attorney, Agent, or Firm* — Ryan, Mason & Lewis, LLP

(57) ABSTRACT

Skin diagnostic techniques employed in conjunction with image processing techniques. For example, a method includes performing one or more diagnostic operations on at least one portion of a user skin image to generate user skin image data, wherein the diagnostic operations are associated with an identified skin-related application. The user skin image data is processed in accordance with the identified skin-related application. The processing includes identifying one or more sets of skin image data in a database that correspond to the user skin image data based on parameters specified by the skin-related application, and determining at least one image processing filter based on the sets of identified skin image data. The image processing filter is applied to the user skin image to generate a simulated user skin image.

38 Claims, 10 Drawing Sheets

(56) References Cited

U.S. PATENT DOCUMENTS

| | | |
|---|---|---|
| 5,944,667 A | 8/1999 | Leveque et al. |
| 5,945,112 A | 8/1999 | Flynn et al. |
| 5,987,351 A | 11/1999 | Chance |
| 6,091,836 A | 7/2000 | Takano et al. |
| 6,097,838 A * | 8/2000 | Klassen et al. ............... 382/167 |
| 6,111,973 A | 8/2000 | Holt et al. |
| 6,292,575 B1 | 9/2001 | Bortolussi et al. |
| 6,293,284 B1 | 9/2001 | Rigg |
| 6,297,420 B1 | 10/2001 | Heincke |
| 6,571,003 B1 | 5/2003 | Hillebrand et al. |
| 6,603,550 B1 | 8/2003 | Flynn et al. |
| 6,681,032 B2 | 1/2004 | Bortolussi et al. |
| 6,807,297 B1 | 10/2004 | Tankovich et al. |
| 6,944,491 B2 | 9/2005 | Leveque |
| 7,035,456 B2 | 4/2006 | Lestideau |
| 7,061,617 B2 | 6/2006 | Querleux et al. |
| 7,104,800 B2 | 9/2006 | Ortiz-Valero et al. |
| 7,130,454 B1 | 10/2006 | Berube et al. |
| 7,218,759 B1 | 5/2007 | Ho et al. |
| 7,233,693 B2 | 6/2007 | Momma |
| 7,336,810 B2 | 2/2008 | Fujii et al. |
| 7,392,204 B1 | 6/2008 | Matsumoto et al. |
| 7,402,135 B2 | 7/2008 | Leveque et al. |
| 7,437,344 B2 | 10/2008 | Peyrelevade |
| 7,454,046 B2 | 11/2008 | Chhibber et al. |
| 7,477,767 B2 | 1/2009 | Chhibber et al. |
| 7,489,960 B2 | 2/2009 | Leveque |
| 7,522,769 B2 | 4/2009 | Harville et al. |
| 7,532,743 B2 | 5/2009 | Morisada |
| 7,558,416 B2 | 7/2009 | Payonk et al. |
| 7,634,538 B2 | 12/2009 | Mori et al. |
| 7,764,303 B2 | 7/2010 | Pote et al. |
| 7,819,311 B2 | 10/2010 | Rowe et al. |
| 7,820,972 B2 | 10/2010 | Miyamae et al. |
| 7,831,072 B2 | 11/2010 | Rowe |
| 7,835,554 B2 | 11/2010 | Rowe |
| 7,840,064 B2 | 11/2010 | Chhibber et al. |
| 7,894,651 B2 | 2/2011 | Gutkowicz-Krusin et al. |
| 7,901,355 B2 | 3/2011 | Querleux et al. |
| 7,916,905 B2 | 3/2011 | Yen et al. |
| 7,916,910 B2 | 3/2011 | Cotton et al. |
| 7,944,689 B2 | 5/2011 | Nelson |
| 7,970,456 B2 | 6/2011 | Preece et al. |
| 7,986,987 B2 | 7/2011 | Bazin et al. |
| 8,026,942 B2 | 9/2011 | Payonk et al. |
| 8,027,505 B2 | 9/2011 | Edgar et al. |
| 8,043,227 B2 | 10/2011 | Van Gogh et al. |
| 8,055,066 B2 | 11/2011 | Xiong et al. |
| 8,094,186 B2 | 1/2012 | Fukuoka et al. |
| 8,109,875 B2 | 2/2012 | Gizewski |
| 8,121,430 B2 | 2/2012 | Corcoran et al. |
| 8,131,029 B2 | 3/2012 | Chhibber et al. |
| 8,139,854 B2 | 3/2012 | Oh et al. |
| 8,150,192 B2 | 4/2012 | Niemeyer et al. |
| 8,155,413 B2 | 4/2012 | Chhibber et al. |
| 8,290,257 B2 | 10/2012 | Demirli et al. |
| 2003/0045799 A1 | 3/2003 | Bazin et al. |
| 2003/0050561 A1 | 3/2003 | Bazin et al. |
| 2003/0067545 A1 | 4/2003 | Giron et al. |
| 2004/0125996 A1* | 7/2004 | Eddowes et al. ............... 382/128 |
| 2004/0218810 A1 | 11/2004 | Momma |
| 2005/0053637 A1 | 3/2005 | Ma'Or et al. |
| 2005/0106103 A1 | 5/2005 | Dussaud et al. |
| 2005/0111729 A1 | 5/2005 | Caisey |
| 2005/0119539 A1 | 6/2005 | Bazin |
| 2006/0029265 A1 | 2/2006 | Kim et al. |
| 2006/0092315 A1 | 5/2006 | Payonk et al. |
| 2006/0129411 A1 | 6/2006 | Bhatti et al. |
| 2006/0229912 A1 | 10/2006 | Negishi et al. |
| 2006/0239547 A1 | 10/2006 | Robinson et al. |
| 2007/0058858 A1 | 3/2007 | Harville et al. |
| 2007/0076013 A1 | 4/2007 | Campbell et al. |
| 2007/0086651 A1 | 4/2007 | Stephan et al. |
| 2007/0092160 A1 | 4/2007 | Fujii et al. |
| 2008/0080766 A1* | 4/2008 | Payonk et al. ............... 382/167 |
| 2008/0130970 A1 | 6/2008 | Niemeyer et al. |
| 2008/0161661 A1 | 7/2008 | Gizewski |
| 2008/0194928 A1 | 8/2008 | Bandic et al. |
| 2008/0212894 A1* | 9/2008 | Demirli et al. ............... 382/276 |
| 2008/0214907 A1 | 9/2008 | Gutkowicz-Krusin et al. |
| 2008/0240606 A1 | 10/2008 | Yamaguchi |
| 2008/0260218 A1 | 10/2008 | Smith et al. |
| 2009/0028380 A1* | 1/2009 | Hillebrand et al. ........... 382/100 |
| 2009/0054744 A1 | 2/2009 | Kitamura et al. |
| 2009/0076639 A1 | 3/2009 | Pak |
| 2009/0141956 A1 | 6/2009 | Chhibber et al. |
| 2009/0196466 A1 | 8/2009 | Capata et al. |
| 2009/0201365 A1 | 8/2009 | Fukuoka et al. |
| 2009/0213379 A1 | 8/2009 | Carroll et al. |
| 2009/0253162 A1 | 10/2009 | Windsor et al. |
| 2009/0327890 A1 | 12/2009 | Mertz et al. |
| 2010/0027002 A1 | 2/2010 | Claps |
| 2010/0105102 A1 | 4/2010 | Hanes et al. |
| 2010/0185064 A1 | 7/2010 | Bandic et al. |
| 2010/0195911 A1 | 8/2010 | Yen et al. |
| 2010/0202673 A1 | 8/2010 | Zhang et al. |
| 2010/0226531 A1 | 9/2010 | Goto |
| 2010/0302358 A1 | 12/2010 | Chen et al. |
| 2011/0016001 A1 | 1/2011 | Schieffelin |
| 2011/0020857 A1 | 1/2011 | Honkonen et al. |
| 2011/0116691 A1 | 5/2011 | Chung et al. |
| 2011/0123703 A1 | 5/2011 | Mohammadi et al. |
| 2011/0134275 A1 | 6/2011 | Nguyen |
| 2011/0164787 A1 | 7/2011 | Legagneur et al. |
| 2011/0206254 A1 | 8/2011 | Patwardhan |
| 2011/0213253 A1 | 9/2011 | Kruglick |
| 2011/0286643 A1 | 11/2011 | Kislal |
| 2011/0300196 A1 | 12/2011 | Mohammadi et al. |
| 2011/0304705 A1 | 12/2011 | Kantor et al. |
| 2011/0317917 A1 | 12/2011 | Free |
| 2012/0008838 A1 | 1/2012 | Guyon et al. |
| 2012/0038787 A1 | 2/2012 | Petrescu et al. |
| 2012/0041282 A1 | 2/2012 | Nichol et al. |
| 2012/0075432 A1 | 3/2012 | Bilbrey et al. |
| 2013/0058524 A1* | 3/2013 | Cohen et al. ............... 382/103 |

FOREIGN PATENT DOCUMENTS

| | | |
|---|---|---|
| WO | PCT/US2014/014886 | 4/2014 |
| WO | PCT/US2014/014891 | 5/2014 |

\* cited by examiner

SKIN DIAGNOSTIC AND IMAGE PROCESSING METHODS

CROSS REFERENCE TO RELATED PATENT APPLICATION

The present application is related to the U.S. patent application 13/859,384 and entitled "Skin Diagnostic and Image Processing Systems, Apparatus and Articles," which is filed concurrently herewith, and the disclosure of which is incorporated by reference in its entirety herein.

FIELD

Embodiments of the invention generally relate to skin diagnostic techniques, and more particularly, to skin diagnostic techniques employed in conjunction with image processing techniques.

BACKGROUND

Skincare or cosmetic visualizations aim to predict and illustrate to a consumer how the consumer's appearance may change in connection with the use of a skincare product or cosmetic treatment. However, the speculative nature of such exercises presents challenges in existing approaches with respect to accuracy and consistency of the visualized consumer results.

That is, a visualization is only as accurate as the data from which the visualization is derived. If the consumer results represented in the visualization are superficially determined based on mere speculation, then such results will not be accurate, and the consumer may become disillusioned with the skincare product or cosmetic treatment.

But even if the projected consumer results represented in the visualization happen to be close to actual results, how accurately the results are visualized can also have a significant effect on whether or not the consumer decides to purchase the skincare product or cosmetic treatment.

SUMMARY

Embodiments of the invention provide skin diagnostic techniques employed in conjunction with image processing techniques.

In one embodiment, a method comprises the following steps. One or more diagnostic operations are performed on at least one portion of a user skin image to generate user skin image data, wherein the one or more diagnostic operations are associated with an identified skin-related application. The user skin image data is processed in accordance with the identified skin-related application. The processing comprises identifying one or more sets of skin image data in a database that correspond to the user skin image data based on one or more parameters specified by the skin-related application, and determining at least one image processing filter based on the one or more sets of identified skin image data from the database. The method further includes applying the at least one image processing filter to the at least one portion of the user skin image to generate a simulated user skin image.

In another embodiment, a system comprises a user information module, a graphical user interface, a skin image database, a processor and an output display. The user information module captures a user skin image. The graphical user interface enables selection of a skin-related application from a plurality of skin-related applications. The processor is coupled to the user information module, the graphical user interface, and the skin image database. Additionally, the processor is configured to determine user skin image data from the user skin image, and identify one or more sets of skin image data in the skin image database that correspond to the user skin image data based on one or more parameters specified by the skin-related application. The processor is also configured to apply at least one image processing filter that corresponds to the one or more identified sets of skin image data from the skin image database to the user skin image to generate a simulated user skin image. The output display, coupled to the processor, displays the simulated user skin image.

Embodiments of the invention can also be implemented in the form of an article of manufacture tangibly embodying computer readable instructions which, when implemented, cause one or more computing devices to carry out method steps, as described herein. Furthermore, other embodiments can be implemented in the form of an apparatus including a memory and at least one processor device that is coupled to the memory and operative to perform method steps.

Other embodiments of the invention can be implemented in the form of means for carrying out method steps described herein, or elements thereof. The means can, for example, include hardware module(s) or a combination of hardware and software modules, wherein the software modules are stored in a tangible computer-readable storage medium (or multiple such media).

Advantageously, illustrative embodiments of the invention provide techniques that leverage detailed skin and product information against image processing capabilities to generate accurate visual estimations for consumers.

These and other objects, features and advantages of the present invention will become apparent from the following detailed description of illustrative embodiments thereof, which is to be read in connection with the accompanying drawings.

DETAILED DESCRIPTION

Embodiments of the invention will be described herein with reference to exemplary computing and imaging system architectures. It is to be understood, however, that embodiments of the invention are not intended to be limited to these exemplary architectures but are rather more generally applicable to any system architectures wherein skin diagnostic techniques can be improved with the use of image compositing techniques such that accurate visual estimations are generated for the skin of a given subject.

As used herein, the term "image" is intended to refer to a rendered image (e.g., an image displayed on a screen), a data set representing an image (e.g., a data set stored or storable in memory), or some combination thereof. Thus, for example, the phrase "user skin image" comprises a rendered image of a portion of user skin, corresponding stored data representing the portion of the user skin, or some combination thereof. In the detailed description to follow, whether an image is being stored or rendered at a given time instance will be evident from the context of the particular illustrative embodiment being described.

As used herein, the phrase "skin-related application" is intended to refer to a diagnostic function or other process associated with the skin of a given subject. By way of example only, such skin-related applications that are embodied by a skin diagnostic and image compositing system as will be described herein may include, but are not limited to, a foundation matching application, a line and wrinkle application, a skin lightening application, a skin evenness application, a skin de-yellowing application, and a de-aging application. The particular application being performed by an application module of the system may be selectable by a user or automatically determined by the system from contextual information obtained and/or derived by the system.

As used herein, the term "module," is intended to generally refer to hardware, software, or some combination thereof, that is configured to perform one or more particular functions in the system. If a module is intended to be implemented specifically as hardware or software, it will be referred to herein as a hardware module or a software module, respectively.

As will be described in illustrative detail below in the context of the figures, embodiments of the invention provide skin diagnostic and image compositing techniques which include, inter alia, obtaining a user skin image to generate corresponding user skin image data, processing the user skin image data against a database in accordance with a skin-related application, and generating a simulated user skin image based on the application of an identified image processing filter(s). Additionally, one or more embodiments of the invention may also include displaying the updated or simulated user skin image in conjunction with a recommendation of one or more relevant skin care products and/or treatment methods.

Figure 1:
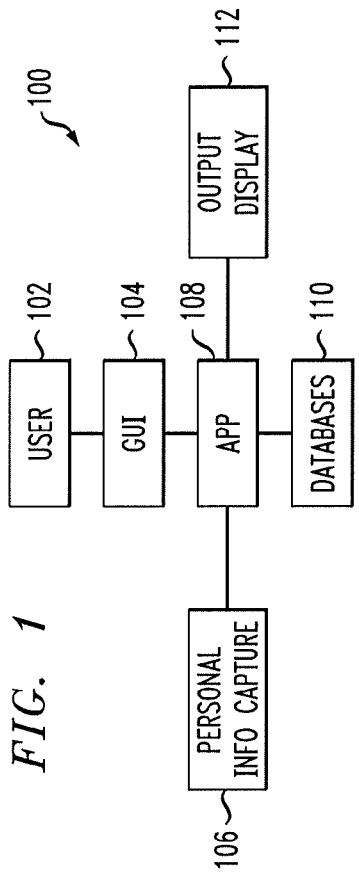
FIG. 1 illustrates a skin diagnostic and image compositing system, according to one embodiment of the invention.

Referring initially to FIG. 1, a skin diagnostic and image compositing system 100 according to one embodiment of the invention is shown. In this embodiment, the system 100 includes a graphical user interface (GUI) 104 (further detailed in connection with FIG. 4 and FIG. 5) which enables a user 102 to access and visually interface with the system. The user 102 is typically the given subject whose skin image(s) is to be captured and processed by the system 100. The GUI 104, in at least one embodiment of the invention, assists in selection of a skin-related application from a plurality of skin-related applications, as well as other system selections. The system 100 also includes a personal information capture module 106 (further detailed in connection with FIG. 3), which is capable of capturing a user skin image, and capturing other user input data. Also, the system 100 includes an application (APP) module 108 (further detailed in connection with FIGS. 7, 8A-8C, and 9), databases 110 (further detailed in connection with FIG. 2), and an output display 112 for presentation of the GUI 104 and any images and other data to the user 102, each of whose functions will be further described below.

In at least one embodiment of the invention, the personal information capture module 106 enables the acquisition of one or more user skin images and other user information. The module 106 may include one or more image capture devices for acquiring an image. The one or more capture devices may include image capture devices capable of capturing images in accordance with different ranges of the electromagnetic spectrum.

By way of example only, the captured images may include, but are not limited to, visible images, infrared (IR) images, and ultraviolet (UV) images. The phrase "visible image" refers to an image captured by a device configured to capture energy in the visible wavelength range of the electromagnetic spectrum. Similarly, an "infrared or IR image" and an "ultraviolet or UV image" respectively refer to images captured by devices configured to respectively capture energy in the IR wavelength range and the UV wavelength range of the electromagnetic spectrum. It is to be understood that the phrase UV images also may include "near UV" images. Further, the phrase "spectral image" refers to images in multiple wavelength ranges including, but not limited to, visible, IR and UV ranges.

Still further, the phrases "RGB image" and "Lab image" are used herein. RGB images are images generated based on the RGB color space model, which is an additive color model in which red, green, and blue light components are added together in different specified proportions to reproduce a broad array of colors. Lab images are images generated based on a color space model with a dimension L for lightness and a and b components representing color-opponent dimensions. The Lab color space model is based on nonlinearly compressed CIE (International Commission on Illumination) XYZ color space coordinates. RGB images and Lab images may be considered visible images. In one or more embodiments, as will be further explained below, RGB values are converted to Lab values, and vice versa, in a known manner.

As is known, ordinary white (visible) light is made up of waves that can travel at all possible angles. Light is considered to be "linearly polarized" when it is composed of waves that only travel in one specific plane. Thus, light waves that travel in a plane parallel to a reference plane of travel are considered parallel light waves, while light waves that travel in a plane perpendicular to the reference plane of travel are considered perpendicular light waves. Thus, as used herein, the phrase "polarized image" refers to an image that is separated into constituent linear polarization components including a "perpendicular light image component" and a "parallel light image component." In contrast, the phrase "non-polarized image" refers to an image that is not separated into such constituent linear polarization components.

As further used herein, the phrase "cross polarization" refers to a polarization condition whereby an image is separated into two components: a "specular component" and an "undertone component." The specular component represents light that reflects off of the surface of the skin, and the undertone component represents light that traverses the surface of the skin and reflects off of a subsurface. In one embodiment, the parallel light image component is comprised of a specular component and half of an undertone component, while the perpendicular light image component is comprised of the other half of the undertone component.

The capture module 106 may also enable the user 102 to enter other information, as well as select one or more previously captured images (viewable via the GUI 104) for processing by the system 100. Additionally, the user 102 can be queried by the system (for example, via the GUI 104) to respond to a series of questions to guide a subsequent analysis of the data corresponding to the captured skin image. Such analysis is carried out in accordance with a selected application via the application module 108. The application can be selected by the user 102 via the GUI 104 or can be automatically determined based on the user responses to the noted queries.

Based on the selected or determined application, one or more relevant portions of the databases 110 are accessed to aid in carrying out the analysis. As further described in connection with FIG. 2 and elsewhere herein, the databases 110 include data pertaining to skin data as well as skincare product data. Accordingly, the databases 110 enable, in accordance with at least one embodiment of the invention, processing of initial user skin image data in accordance with one or more corresponding user parameters to determine the behavior of a particular skincare product or treatment over a period of time within the context of the user skin image data.

Also, as described further herein, the application module 108 includes a processor module (not expressly shown in FIG. 1 but which is further described below in connection with FIG. 11 and FIG. 12) coupled to the personal information capture module 106, the GUI 104, the databases 110 and the output display 112. In at least one embodiment of the invention, such a processor module is configured to determine user skin image data from the user skin image, identify sets of skin image data in the databases that correspond to the user skin image data based on parameters specified by a skin-related application, and apply at least one image processing filter that corresponds to the identified sets of skin image data (from the skin image database) to the user skin image to generate a simulated user skin image.

The output of the analysis is generated for presentation on the output display 112 and includes an updated/simulated image and/or a changing series of simulated images. Such an output can include a visualization of the initial user skin image (e.g., user skin image prior to skin diagnostic operations being performed by the system 100) as well as a visualization representing how that image would change over a selected period of time, based on the severity of the queried variables in the user image contrasted against the severity of those variables in the relevant databases in relation to corresponding parameters such as age, race, gender, etc. It is noted that because different variables may change or evolve at different rates depending on initial severity and one or more corresponding parameters, such an analysis may not present a linear process. As such, an embodiment of the invention includes generating and leveraging relevant non-linear curves in connection with processing user skin images with one or more databases.

Accordingly, the system 100 is generally configured to acquire or select a skin image, process the skin image to obtain relevant skin image data, process the skin image data against one or more relevant databases to determine pertinent skin image data corresponding to a selected diagnostic application, and output a resulting set of simulated skin image data to a display.

Details of how the system 100 is able to perform these and other steps and operations are described below in connection with FIG. 2 through FIG. 12.

Figure 2:
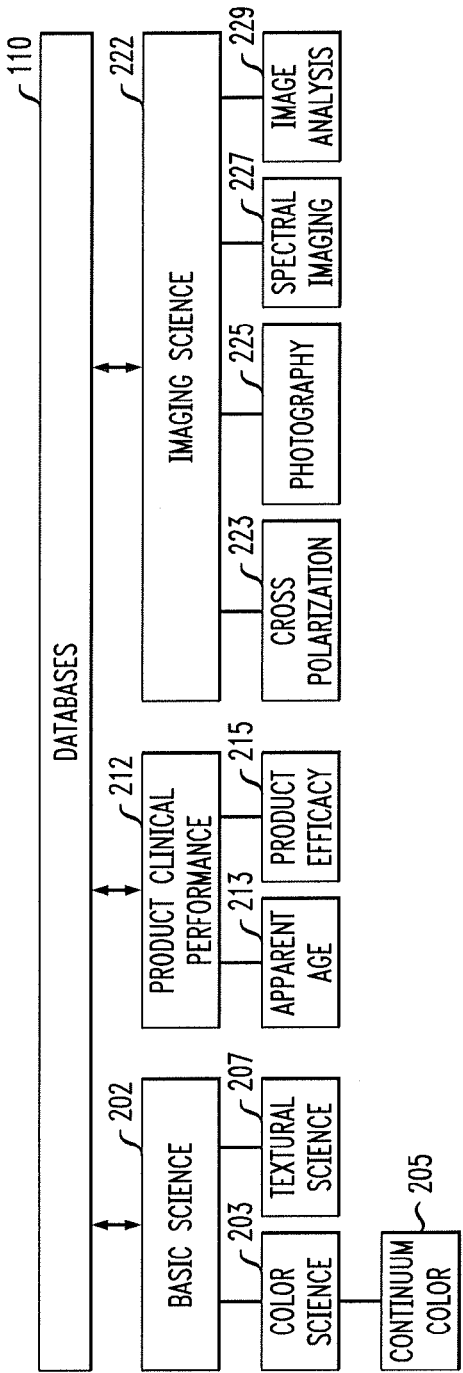
FIG. 2 illustrates details of a database environment employed by a skin diagnostic and image compositing system, according to one embodiment of the invention.

FIG. 2 shows a database environment which may be employed by a skin diagnostic and image compositing system according to one embodiment of the invention. While FIG. 2 illustrates different types of separate databases with different functional labels, it is to be appreciated that this is for illustration purposes only. That is, the data described herein as being part of the database environment 110 may be stored, accessed, and otherwise managed in one or more conventional database structures without regard to the specific functional purpose of the data.

By way of example, FIG. 2 depicts the databases 110 (FIG. 1), which include, but are not limited to, databases pertaining to basic science data 202, product clinical performance data 212, and imaging science data 222. As further detailed below, the basic science databases 202 include databases pertaining to color science data 203, which also includes continuum of color data 205, and textural science data 207. The phrase "continuum of color," as will be further explained below, refers to a color palette comprising all known types of skin colors. Similarly, the product clinical performance databases 212 include databases pertaining to apparent age data 213 and proprietary product efficacy data 215. The phrase "apparent age," as will be further explained below, refers to changes seen with respect to skin as a result of age and ethnicity and is contrasted with the phrase "chronological age." Also, the imaging science databases 222 include databases pertaining to cross polarization image data 223, photography data 225, spectral imaging data 227 and image analysis data 229. The imaging science databases 222 may also include product color information.

It is to be appreciated that at least a portion of the data in the above databases 110 is compiled from images (for example, but not limited to, facial images) captured from a large number of human test subjects. The images include images covering a wide range of varying human demographics such as, for example, age, race, ethnicity, gender, geographic origin, etc. Data compiled from these images can include skin color data, skin texture data, etc., as will be further explained below. Thus, the data in the databases 110 includes images, information derived from such images, and information used to derive other information usable by the system 100.

The data in databases 110 is to be distinguished from data captured or otherwise obtained from a user of the system 100. That is, the data in databases 110 is predominantly data previously obtained from test subjects and other sources that is compiled for use in performing the selected diagnostic operations on a skin image provided by a current user 102 of the system 100. However, it is to be understood that data from the current user 102, subject to their approval, may become part of the data in databases 110 and used for a subsequent user 102.

Additionally, the images in the databases 110 may include images that are linked to specific skin conditions, as well as images that are linked to specific skincare products and/or treatments. In at least one embodiment of the invention, a skin-related application is identified via specification of a skin product and/or a skin product category (data associated therewith which is stored in one or more of the databases). Skincare product data can include, for example, age-related skin image data and skincare product efficacy data. Additionally, parameters specified by a skin-related application can include, by way of example, a severity-time parameter based on information (e.g., stored in product clinical performance database 212).

Furthermore, the databases 110 include spectral imaging data (e.g., stored in spectral imaging database 227). Spectral imaging data includes, but is not limited to, a plurality of two-dimensional digital spectral images of human skin that are captured from a variety of human subjects and stored (and categorized) in the database. A spectral image as mentioned above refers to image data captured at different wavelength ranges across the electromagnetic spectrum. Such spectral images can include visible images, as mentioned above, as well as images captured at wavelengths that allow extraction of additional information that the human eye fails to capture with its receptors for the red, green and blue (RGB) light components, e.g., infrared images, ultraviolet images, etc. Each spectral image stored in the database defines a target area of skin. By way of example only, such digital spectral images may be captured and stored in a manner described in International Publication No. WO2011/112422, entitled "System for Skin Treatment Analysis Using Spectral Image Data to Generate 3D RGB Model," filed on Mar. 3, 2011, and commonly owned by the assignee of the present application, the disclosure of which is incorporated by reference herein in its entirety.

Thus, a corresponding plurality of two-dimensional digital RGB (red, green, blue) color model images are captured and stored in the databases 110 (e.g., image analysis database 229). Each of the RGB images corresponds at least in part to at least one of the spectral images defining a target area of skin. During processing for user 102, as will be further explained below, a portion (or all) of the plurality of spectral images are analyzed to identify within the respective spectral image one or more spectral image datasets. As used herein, a spectral image dataset refers to the minimum amount of spectral image digital data required to uniquely define a condition of the skin, as, for example, associated with a particular variable or parameter such as skin type, blood or melanin level, oxygen saturation, percent hemoglobin, percent water or moisture content, etc.

As discussed herein in connection with one or more embodiments of the invention, the selected or defined skin condition may be a skin condition not needing treatment or correction, or the skin condition may be a treatable or correctable skin condition such as, for example, dry, oily, cracked, and other treatable, correctable skin conditions. In any case, the spectral image datasets define one or more such skin conditions.

As noted, each element within each image is recorded and indexed based, for example, on pixel coordinates on the image, RGB values of the pixel and/or spectral content of the pixel, and type of skin condition at that pixel. Accordingly, each skin condition is mapped to one or more pixels in the respective image. More specifically, each spectral image dataset is mapped to a location within the respective spectral image (referred to herein as the spectral location). That is, a spectral location includes the pixel coordinate location within a spectral image for a spectral image dataset. In an RGB image corresponding to a respective spectral image, a location is mapped that corresponds to each spectral location. The location in the RGB image is referred to herein as the RGB location; that is, the pixel coordinate location within an RGB image that corresponds to a spectral location in a respective spectral image.

Additionally, as used herein, an RGB dataset refers to the minimum amount of digital RGB data required to uniquely identify an RGB color profile associated with that respective location. Accordingly, in at least one embodiment of the invention, the spectral image dataset is effectively correlated to an RGB dataset that corresponds to at least one known skin condition defined by said spectral image dataset. Also, an RGB dataset is created, pixel-by-pixel, from each spectral image dataset by passing the spectral image data through a conversion function with the area under each resulting curve being summed to provide the RGB dataset. The spectral curve for each pixel in the spectral image dataset for a specific subject is fit, using known curve fitting methods, to reveal the details of the skin biology and chemistry. One parameter, melanin concentration, is uniquely tied to the whitening behavior of certain products. In order to simulate such whitening effects of a product by the alteration of melanin concentrations in skin, the spectral image dataset at each pixel is first divided by a function $R_{mel}(\lambda)$ which describes the reflectance of melanin at the particular concentration of melanin x for that subject. This results in a "melaninless" spectral curve, which is multipled by the new melanin curve, which is found by a function $RN_{mel}(\lambda)$. Before $RN_{mel}(\lambda)$ can be calculated, the change in melanin concentration is found by using a data chart (e.g., such as the one in FIG. 8A, which will be described in further detail below) which represents the change in melanin due to product use, this is then multiplied by x to create a new x, i.e., x=x*% change, as will be further described below in the context of FIGS. 7 through 9.

The function which describes $R_{mel}(\lambda)$ and $RN_{mel}(\lambda)$ is $EXP^{\wedge}(0.012x*MUA_{mel}\lambda*(4.51-Log_{10}(x*MUA_{mel}\%))$ where x is the average melanin concentration at a specific timepoint of interest and $MUA_{mel}$ represents the known absorbtion curve of melanin. This new curve is then multiplied by the "melaninless" curve to create the new spectral curve at the new melanin concentration. This process yields a spectral image dataset with the altered melanin concentration. The spectral image dataset is then converted to an RGB image dataset.

The conversion function for transforming the spectral image dataset to an RGB dataset involves multiplying the spectral image dataset by individual R, G, and B spectral response functions, and subsequently summing the area below the curve for each and then dividing each by the respective area below the curve of each corresponding spectral response curve. This results in values for R, G, and B that yields the color image in RGB color space. The spectral response function is obtained by spectral imaging of standard R, G and B color reference targets with a spectral camera. In this manner, a series of images are created which simulates the effects of whitening from product usage over time related to melanin concentration. The general RGB conversions for whitening at each timepoint are then found in a straightforward manner by dividing the average RGB values of an average area of the starting image by the corresponding average area in each simulated image, i.e., using the specific x calculated from the data in a melanin percentage change chart (e.g., FIG. 8A). Once these conversion factors are known, these conversion factors are used to simulate whitening effects for subjects whose starting average melanin concentration is similar to the those of the reference subject who was subjected to full spectral imaging.

The conversion function is optimized from the minimization of the differences between the measured RGB values in RGB space and those values calculated from the transformation RGB of the spectral dataset. Accordingly, in at least one example embodiment of the invention, a virtual look-up table (LUT) between the RGB dataset and the spectral image dataset is established that is representative across all spectral image datasets. Such mappings and LUTs are stored in the databases 110 (e.g., stored in the spectral imaging database 227, the image analysis database 229, or a combination thereof).

Advantageously, different skin conditions are catalogued in spectral datasets and correspond to determinable reference RGB datasets. The captured spectral images and corresponding captured RGB images are compiled and stored along with the spectral image datasets representing skin conditions, the spectral locations, the RGB locations and the reference RGB datasets.

Still further, in one or more embodiments, the RGB datasets are converted to Lab datasets such that the different skin conditions are catalogued in spectral datasets that correspond to determinable reference Lab datasets.

Still referring to FIG. 2, the databases 110 include RGB/Lab values corresponding to a wide range of human races and ethnicities (e.g., stored in the continuum of color database 205). Such data represents RGB/Lab distribution from one geographic region to another geographic region, how particular RGB/Lab values change with age, etc.

Additionally, the databases 110 includes data that indicates how physical properties such as wrinkles, pores, fine lines, dark circles, reddening in the cheeks, elasticity of the skin, etc. change and vary in different demographic groups (e.g., stored in the textural science database 207).

As also noted above, the databases 110 include data pertaining to product clinical performance (e.g., stored in databases 213 and 215). Apparent age data (e.g., stored in database 213) contains data and models that are used to assign an apparent age, as compared to a chronological age, to a person. The phrase "chronological age" or actual age refers to the age of a person in terms of the person's actual life span. The phrase "apparent age" refers to the age that a person is visually estimated or perceived to be, based on their physical appearance, particularly the overall appearance of the face. Chronological age and apparent age are generally measured in years and parts thereof. One goal of anti-aging skincare products is to reduce apparent age relative to chronological age, preferably reducing apparent age below chronological age, so that a person appears younger than their actual age. Products that achieve this goal are able to prevent skin damage and/or remove damage induced by age-promoting factors. By way of example only, such apparent age data and models may be generated and stored in a manner described in International Publication No. WO2010/028247, entitled "An Objective Model of Apparent Age, Methods and Use," filed on Sep. 4, 2009, and commonly owned by the assignee of the present application, the disclosure of which is incorporated by reference herein in its entirety.

Product efficacy data (e.g., stored in database 215) includes data that indicates how certain skincare products and treatments behaved and/or reacted in connection with various types of human skin over varying periods of time and treatment regimens. More specifically, skincare products and treatments are composed and/or arranged in certain manners and with certain sets of ingredients or components so as to target and/or treat one or more particular skin conditions (for example, reduce or remove wrinkles, lighten skin tone, even-out skin tone, etc.). Such information is included in the product efficacy database 215, along with data pertaining to the corresponding targeted objectives of the product or treatment.

Data that describes the uniformity, radiance, or dullness of the skin, or the location and size of different types of spots, including age spots, freckles, etc. (below the skin) is stored in the databases 110 (e.g., cross polarization database 223). Data describing the location, size, severity, and length of wrinkles, and the location, size, severity and diameter of pores is also stored in the databases 110 (e.g., photography database 225).

Figure 3:
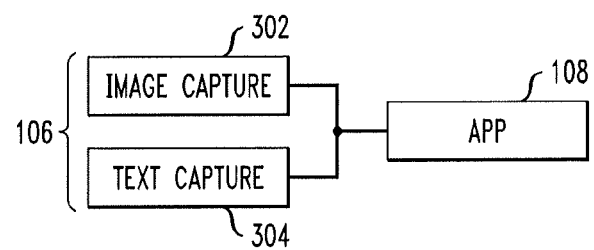
FIG. 3 illustrates details of a personal information capture module of a skin diagnostic and image compositing system, according to one embodiment of the invention.

FIG. 3 shows a personal information capture module of a skin diagnostic and image compositing system according to one embodiment of the invention. By way of illustration, FIG. 3 depicts a personal information capture module (such as depicted as module 106 in FIG. 1) that includes an image capture module 302 and a text capture module 304.

In at least one embodiment of the invention, the image capture module 302 includes, for example, one or more image capture devices for acquiring an image. For example, the one or more capture devices may include image capture devices capable of capturing images in accordance with different ranges of the electromagnetic spectrum, e.g., visible images, infrared images, and ultraviolet images. That is, module 302 includes one or more digital cameras capable of capturing visible images, and one or more cameras, devices and sensors capable of capturing images in other electromagnetic spectrum wavelength regions (e.g., infrared, ultraviolet, etc.). In one embodiment, the camera is a polarization-enabled camera which is configured to capture three image components: parallel, perpendicular, and non-polarized. One or more of the image capture devices are also preferably configured to capture specular image components and undertone image components, as described herein with regard to cross polarization embodiments.

Additionally, the text capture module 304 can include, for example, a keyboard or keypad for manual text input, and/or a device configured for automatic speech recognition (ASR) such as a speech-to-text (STT) module.

The captured and/or compiled information is used to analyze skin conditions of an individual subject or user by comparing datasets derived from the images to reference datasets in the databases 110 depicted in FIG. 2. Additionally, upon and/or in conjunction with the capture of information (as depicted in FIG. 3), one or more embodiments of the invention include providing the user with a specific set of queries (for example, a default set of queries and/or a custom set of queries tailored to the user) to begin a diagnostic process. Such queries are presented, for example, on output display 112 via GUI 104 shown in FIG. 1. The queries may include, but are not limited to, questions and/or other forms of prompts guiding the user to select one or more diagnostic regions, one or more skincare products or services, one or more time-points, one or more average methods/modes, one or more match modes, one or more application modes, and one or more color shades, which will each be explained in further detail below with respect to illustrative embodiments of the application module 108.

Figure 4:
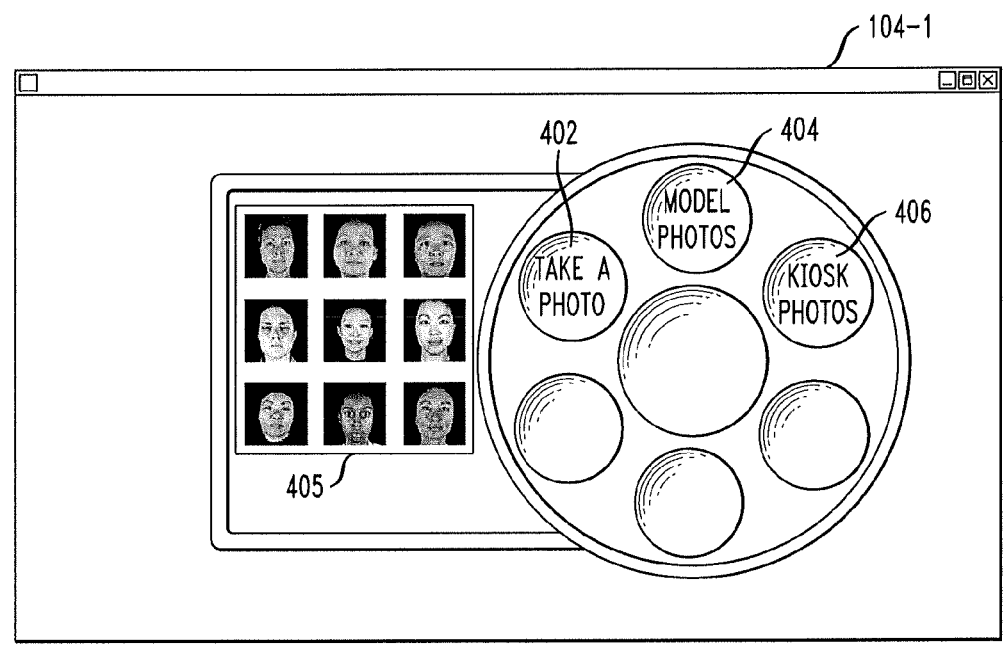
FIG. 4 illustrates a first portion of a graphical user interface of a skin diagnostic and image compositing system, according to one embodiment of the invention.
Figure 5:
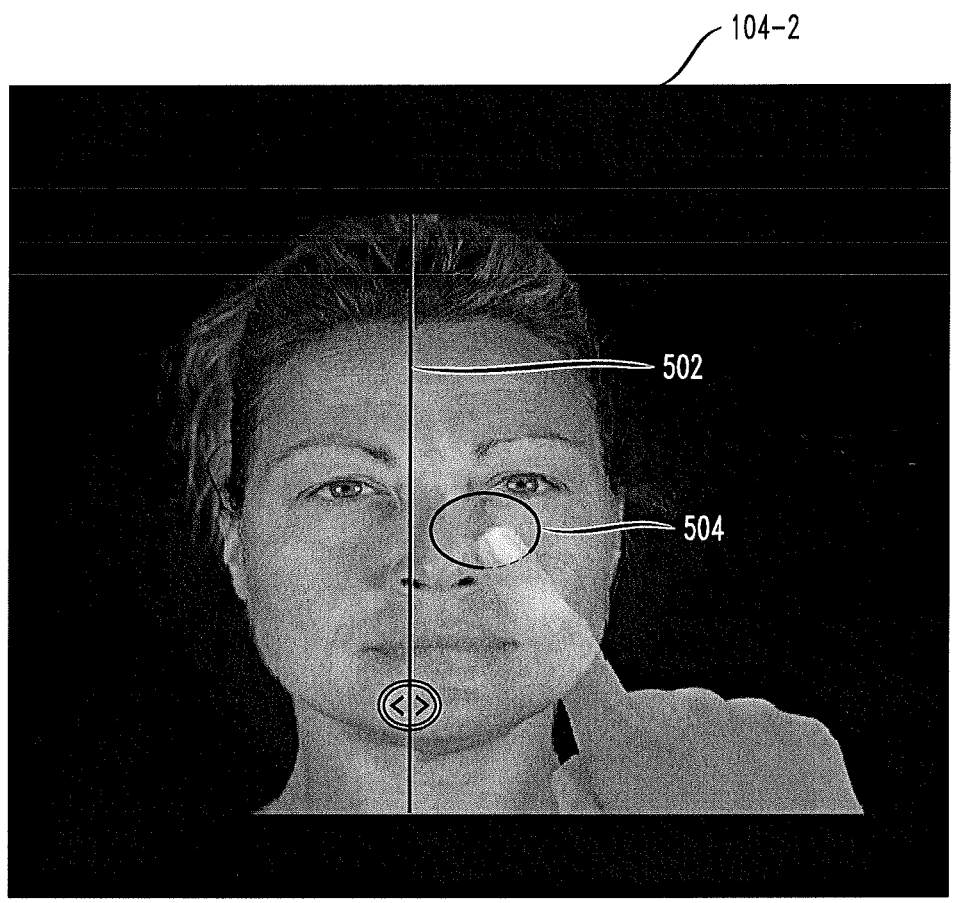
FIG. 5 illustrates a second portion of a graphical user interface of a skin diagnostic and image compositing system, according to one embodiment of the invention.

FIGS. 4 and 5 are examples of screenshots that are displayed by the system 100 to the user on GUI 104. It is to be understood that these GUI examples are merely to illustrate a portion of the features and functions of the system, and are not intended to be limiting in any way. Given the inventive teachings herein, one of ordinary skill in the art will realize many other varied features and functions that can be presented to a user via the GUI 104 in a straightforward manner.

FIG. 4 illustrates a first portion of a graphical user interface 104-1 of a skin diagnostic and image compositing system, according to one embodiment of the invention. As detailed herein, an example embodiment of the invention is implemented in a kiosk environment. In such an embodiment, the kiosk is designed for use at, for example, a retail location or counter, and can be contained within the context of a larger enterprise operation. An example kiosk environment may include lighting devices (to provide appropriate lighting for capturing images), a processor running one or more applications to control an image capturing device (such as a camera), and a display (with touch screen) such as depicted in the GUI 104-1 in FIG. 4. Again, the kiosk-based system at the retail location may be in communication with a backend system. An exemplary processing platform for realizing the kiosk-based system will be further described below in the context of FIG. 12.

As shown, the GUI 104-1 includes touch screen-enabled selection features 402, 404 and 406. Such features enable the user to direct the system to capture his/her own image (or "photo") via feature 402, or connect to a system database and upload a pre-existing image from either a set of models 405 (via feature 404) or other kiosk users (via feature 406).

Accordingly, in the example implementation of a retail location, a user or customer has his or her photograph taken at a kiosk, the photograph is analyzed in accordance with the system 100, and an advisor or other enterprise personnel subsequently provides diagnostic results and/or recommendations generated by the system 100 away from the kiosk via a tablet or other device configured according to enterprise preference or specifications. Of course, the results and/or recommendations may be presented directly to the user or customer without the need for an advisor or other personnel.

FIG. 5 illustrates a second portion of a graphical user interface 104-2 of a skin diagnostic and image compositing system, according to one embodiment of the invention. As shown, by way of example only, GUI features provide capabilities such as manipulation of the user skin image via at least one of a before/after swiper feature 502. With the swiper feature, a user can simultaneously see what one portion of his/her face looks like before a specific skincare product treatment and what another portion of his/her face looks like after the specific treatment, e.g., see vertical line 502 running down user's face providing the comparative skin conditions. The user can move the line 502 in a swiping motion to change what part of the face is shown as being treated and which part is not.

Additionally, another GUI feature includes a zoom-in and/or zoom-out feature for shrinking or enlarging a portion of the user skin image, and localized inspection of images. That is, the user is able to point to a specific facial area in the image and have that location enlarged (and then shrunk again) within a window such as the circular window labeled 504.

Further, GUI features may also include a contrast feature, as well as a lighting simulation feature so as to, for example, simulate daylight or incandescent lighting. Still further, GUI features may include a foundation finder "wand" or selection feature to redefine a diagnostic sampling area for determining foundation shades. It is to be appreciated that the GUI 104 may provide the user 102 with any known image manipulation features (not expressly shown) that would aid in the diagnostic operations of the system, as well as aid in increasing the positive experience the user has with the system.

Such GUI features can, for example, be implemented in the form of active buttons on the user interface, via a pop-up tool bar on the user interface, etc. Further, in at least one embodiment of the invention, additional options on the GUI include links to external sites and sources such as various e-commerce enterprises, global positioning systems, social networks, etc.

Figure 6A:
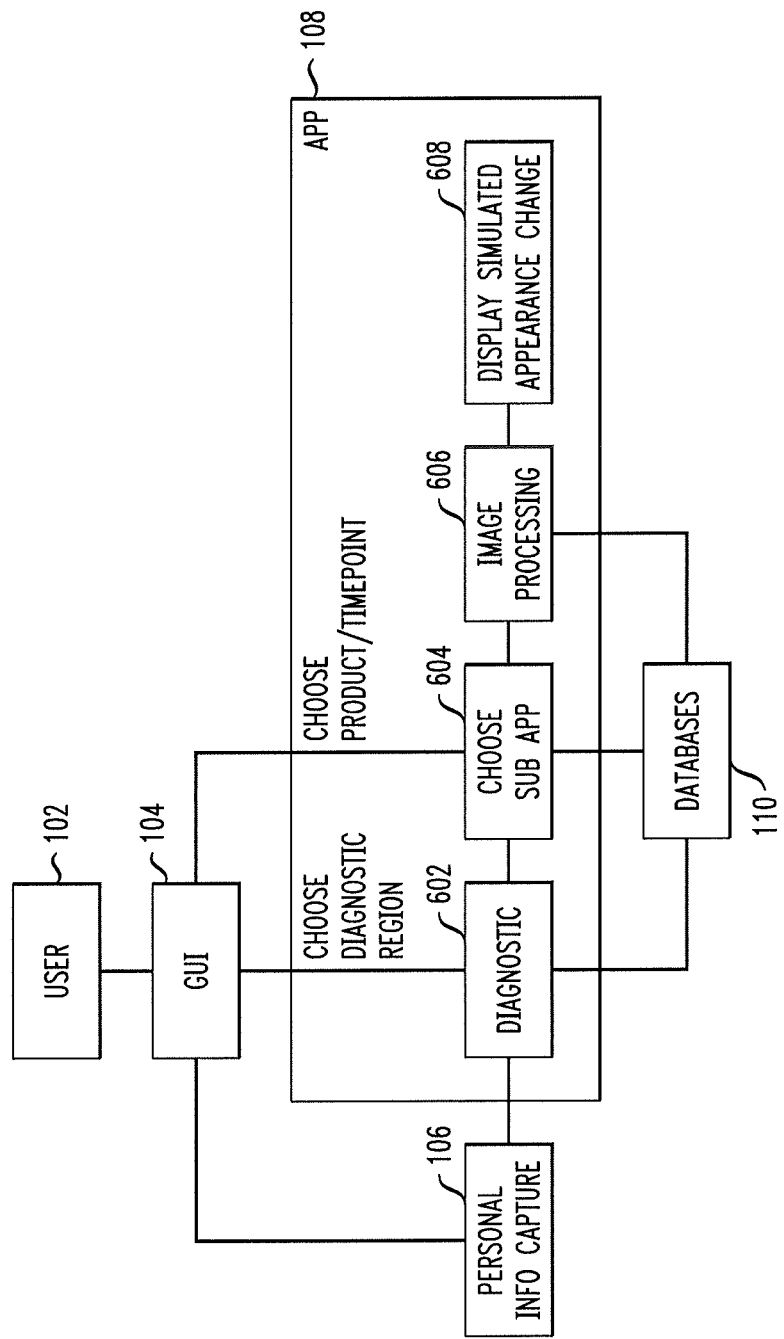
FIG. 6A illustrates details of an application module of a skin diagnostic and image compositing system, according to one embodiment of the invention.

FIG. 6A illustrates details of an application module 108 of a skin diagnostic and image compositing system, according to one embodiment of the invention. As shown, application module 108 includes a diagnostic module 602, a sub-application selection module 604, an image processing module 606, and a simulated appearance change display module 608. More particularly, FIG. 6A shows details of how the application module 108 operates when processing data captured or otherwise obtained from a current user 102 of the system 100.

Figure 6B:
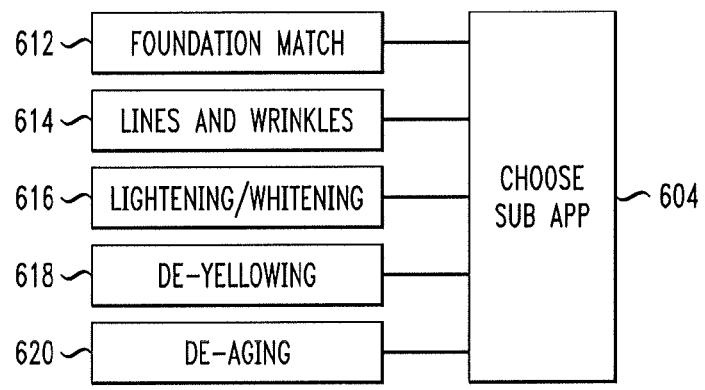
FIG. 6B illustrates details of a sub-application selection module of a skin diagnostic and image compositing system, according to one embodiment of the invention.

In connection with the depiction in FIG. 6A, at least one embodiment of the invention includes enabling selection of a skin-related application from a plurality of skin-related applications (see, for example, FIG. 6B). It is to be appreciated that the terms "application" and "sub-application" are interchangeable as used herein. In this example, the sub-applications referred to in FIGS. 6A and 6B are skin-related applications and are referred to here as sub-applications given that they are applications selectable in the application module 108. As shown in FIG. 6B, examples of sub-applications include, but are not limited to, a foundation matching application 612, a lines and wrinkles application 614, a skin lightening application 616, a skin de-yellowing application 618, and a de-aging application 620. Each of these sub-applications will be described in further detail below. However, embodiments of the invention are not intended to be limited to any particular sub-application or set of sub-applications.

Accordingly, the diagnostic module 602, in conjunction with the sub-application selection module 604, is configured to determine one or more conditions that need correcting on the user's skin from the one or more images captured of the user. Then, based on the diagnosed problem, the appropriate sub-application is selected. The user can specify a skin region that he/she wishes to be diagnosed by the system. Alternatively, the system can automatically find the problem region(s). Still further, the user can directly specify what sub-application he/she wishes to engage. In any event, a diagnostic region is chosen, and a sub-application is selected in accordance with modules 602 and 604.

Once the sub-application is chosen, the sub-application operates in conjunction with data in the database environment 110, as described above, to generate an image (or set of images) via the image processing module 606 that represents results of the particular diagnostic operations performed in accordance with the chosen sub-application. The image (simulated appearance change image) is displayed via module 608 (through GUI 104 and output display 112 in FIG. 1).

Figure 7:
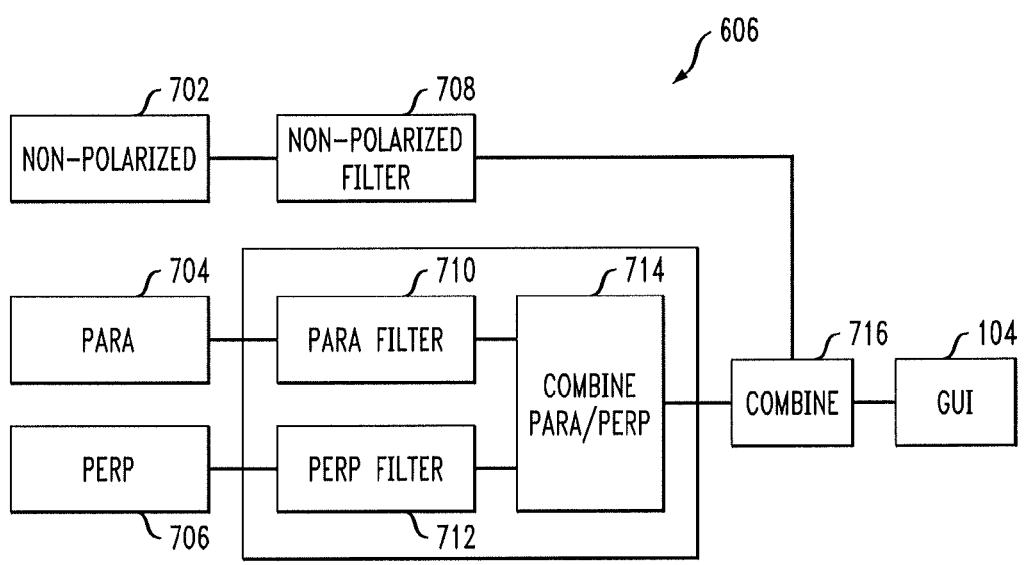
FIG. 7 illustrates details of an image processing module of a skin diagnostic and image compositing system, according to one embodiment of the invention.

FIG. 7 illustrates details of the image processing module 606. In general, the image processing module 606 operates on an image (image components as shown on left hand side of in FIG. 7) to generate a simulated user image that is displayed to the user. The image that is operated on by module 606 is the image captured by capture module 106, i.e., a user skin image. In this embodiment, it is assumed that the user skin image is represented as a non-polarized image component 702, a parallel light image ("Para") component 704 and a perpendicular light image ("Perp") component 706 from the user skin image. Alternatively, the image that is operated on by module 606 could be a sample image that the user selects via the GUI 104 (recall the model image selection feature on GUI 104-1 in FIG. 4). Presumably, the user may select this sample image to use as a demonstration to view the results of some diagnostic operation on the sample image, rather than the user providing his/her own image. Regardless of whether the image is the user image or a sample image, it is operated on by the image processing module 606 in the same or a similar manner. Also, as mentioned above in one embodiment, the parallel light image component 704 is comprised of a specular component and half of an undertone component, while the perpendicular light image component 706 is comprised of the other half of the undertone component. This is the case when cross polarization is employed to capture and process the user's skin image.

As shown in FIG. 7, the image processing module 606 determines a non-polarized image filter 708, a parallel light image filter 710, and a perpendicular light image filter 712. Note that the three filters 708, 710 and 712 shown in FIG. 7 may be referred to cumulatively as "an image processing filter" or individually as separate filters. The filters are determined as follows. Recall that databases 110 include one or more look-up tables (LUT) of spectral datasets correlated to RGB datasets that were previously established by compiling test data from subject populations. Thus, the image processing module 606 obtains an RGB image captured from the user 102, normalizes (or standardizes) the RGB image (for example, via standard profiling software) to calibrate color, intensity, etc., and compares the normalized datasets of the RGB image to the LUT to determine corresponding spectral image data sets, and in turn, the skin conditions associated with the spectral image datasets. Recall that, in one embodiment, the LUT stores Lab datasets corresponding to spectral image datasets. In such a case, the RGB values of the user image are converted to Lab values before performing the look-up operations.

The image processing module 606 applies: (i) the non-polarized image filter 708 to the non-polarized image component 702 to generate a proscenium image component; (ii) the parallel light image filter 710 to the parallel light image component 704 to generate a simulated parallel light image component; and (iii) the perpendicular light image filter 712 to the perpendicular light image component 706 to generate a simulated perpendicular light image component. The simulated parallel light image component and the simulated perpendicular light image component are combined in a first combination module 714, for example, using the equation (Para+Perp)/2, to generate a base simulated user image for the skin-related application. The base simulated user image is combined with the proscenium image component in a second combination module 716 to generate the simulated user skin image. The combination operations are referred to herein as "image compositing," a visual example of which will be described below in the context of FIG. 9. The simulated appearance change display module 608 subsequently outputs the simulated user skin image to the output display 112 in FIG. 1 for presentation via GUI 104 to the user.

Recall that databases 110 contain data describing a large range of facial features (e.g., pore size, wrinkle lengths and widths, age spots, skin color, skin whitening/yellowing, skin uniformity, under eye dark circles, etc.) as a function of natural aging and specific product effects. The data includes average values as a function of age and average values of the time effects of products. Hence, these numerical sequences represent a record of how the average skin changes for that specific feature, either as a direct function of aging or as a result of the specific product application time. This data has been compiled over time by research and clinical scientists, using physical measurements (e.g., photographic, etc.) and expert panel assessment of photographic imagery.

As such, image processing module 606 obtains the polarized image components (parallel light image component 704 and perpendicular light image component 706) for the subject user and the corresponding filters (710 and 712) then transform the image components on a pixel by pixel basis such that the resultant combined non-polarized image visually matches the expected overall average time behavior of the particular product. The image transforming filters 710 and 712 are created using photographic reference and physical measurement information from the databases 110. These filters perform mathematical transformations on each pixel such that the resultant transformed polarized images, when combined into the non-polarized image, give the realistic rendering of a product's average behavior at a particular time.

It is to be undrstood that the image filter 708 is driven by facial reconignition where the face is automatically located, and the eyes, nose, lips, hair, and the edge of the face are then located. All other parts of the image component that are not a part of these located areas are made transparent and used to create the proscenium image, which allows the background to remain constant as well as the eyes, nostrils, and lips which do not change during a skin treatment application. In one embodiment, the filtered parallel and perpendicular image components are combined by use of the equation (Para+Perp)/2 to create the displayable facial image.

Figure 8A:
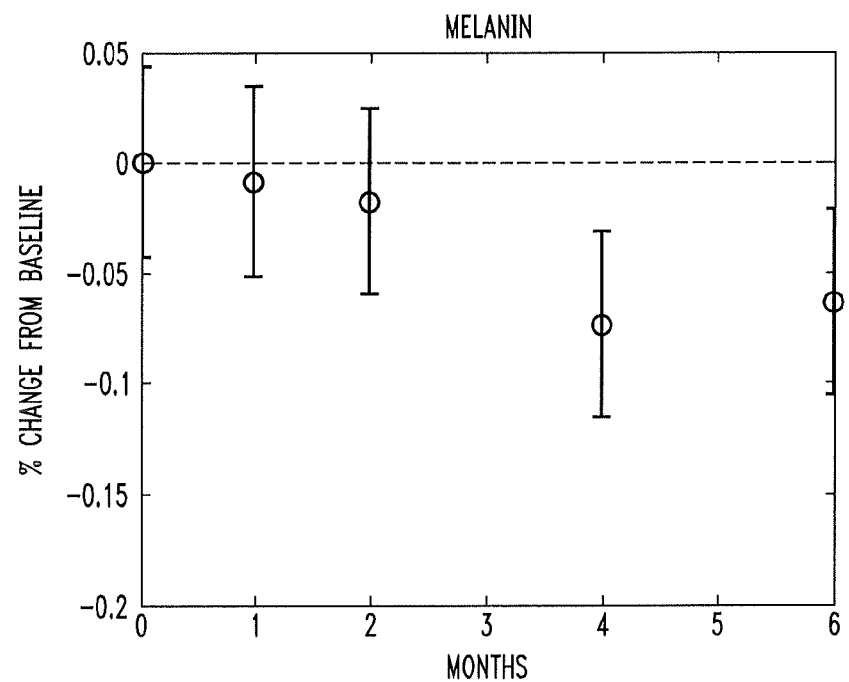
FIG. 8A through 8C illustrate graphical representations of percent changes of certain skin parameters over specific timepoints, according to embodiments of the invention.
Figure 8B:
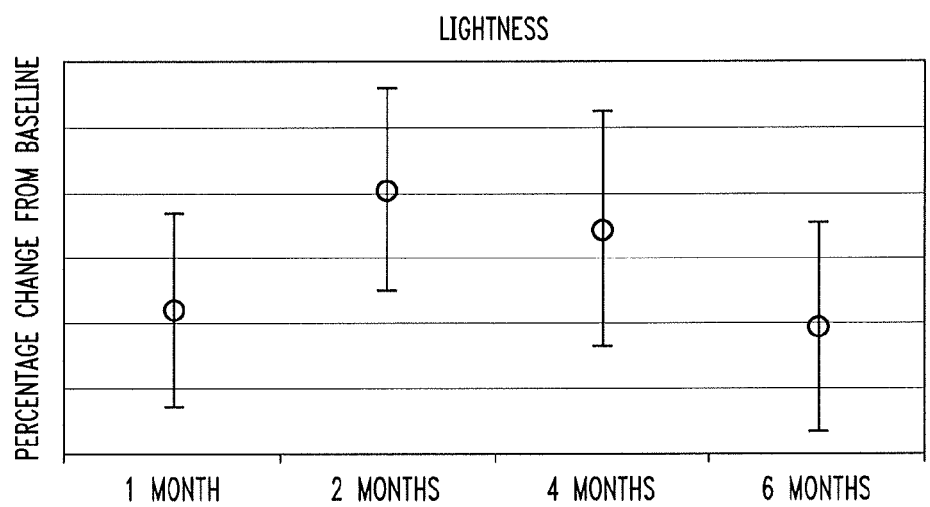
Figure 8C:
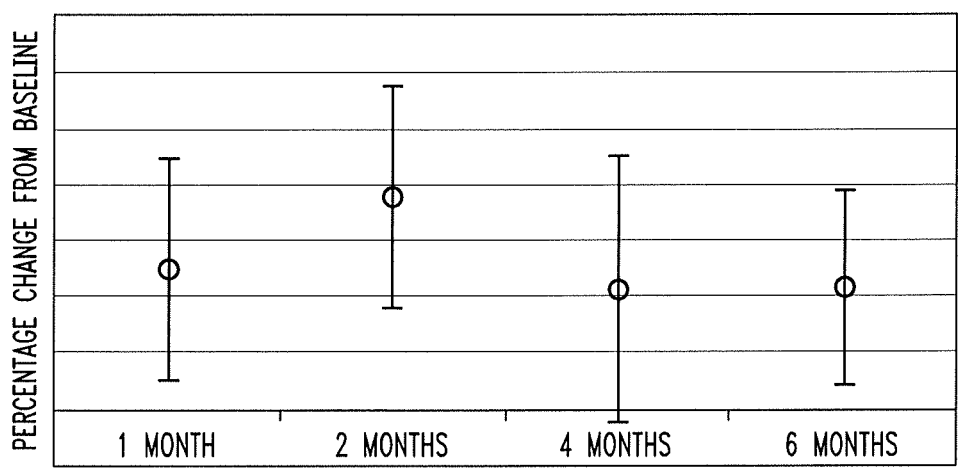

As an example, the function that describes the time varying behavior of a whitening skincare product relies on physical measurements that determine the change in skin color over time. Expert panel assessments of photographic images have been acquired for these products, which yield qualitatively similar trends to the physical measurements. However, exact color measurements can be used. For these whitening products, the average values of L, a, and b show a modulation over time yielding a function that describes the average change for a given skin parameter, see FIG. 8A (i.e., melanin as the skin parameter), FIG. 8B (i.e., lightness as the skin parameter), and FIG. 8C (i.e., yellowness as the skin parameter). As an example, FIG. 8A shows the average change in melanin for a particular study group. Each subject has a melanin value which is calculated at each timepoint. Then, using the equation Percentage Change=((TimePoint−Baseline)/Baseline) *100, the specific change in melanin for each subject is calculated. The entire group is then averaged and the data then stored in databases 110 mentioned above. This information is used then to directly modulate the color over time in the polarized image components (704 and 706) for the subject user starting from his/her own values determined from his/her captured image. The Lab values of the captured polarized image components are directly adjusted by using the average amount of change at any given timepoint given by the RGB/Lab-to-spectral image data LUT in databases 110. In one embodiment, the Lab values for the perpendicular image component 706 are adjusted by the exact change given in the LUT, while the Lab values for the parallel image component are adjusted by a fraction of the exact change to correspond to visually realistic and corresponding non-polarized images. Such fractional component contribution is determined for each of the three color layers in the RGB dataset. In one embodiment, the experimental values for lightening are determined in a cross polarized manner (as explained above) and thus reveal information for the perpendicular component only. It was found empirically that, in order to create a realistic representation for a transformed non-polarized image, a preferred correspondence is achieved by modulating the parallel image component by half the change as measured for penetrating light (i.e., the perpendicular polarization component).

In accordance with an alternative embodiment of the invention, a methodology is provided to create a simulation of the continuous change of facial appearance over time (de-aging or a product effect) as a sequence of images, similar to a scrolling or of a playing movie. The methodology, in one embodiment, incorporates five timepoint changes, however, this could be any number of timepoints. In this alternative method, the initial captured polarized image components ("Para initial" and "Perp initial") are mixed with polarized image components ("Para final" and "Perp final") and subsequently combined to form the non-polrized image for any given time point. "Para final" and "Perp final" are created from the initial polarized image components, by changing the image components to reflect an overall product endpoint, or by zeroing out the specific facial features to bring a person back to their pre-aging youthful state. To a first approximation, a linear mixing of the images is used. "Para Initial" is combined with "Para Final," following the equation ParaInitial(1−T)+ParaFinal(T)=ParaTransformed at timepoint T. "Perp Initial" is combined with "Perp Final," following the equation PerpInitial(1−T)+PerpFinal(T)=PerpTransformed at timepoint T. T corresponds to normalized time and lies between zero and one, T=1 is final time. This linear mixing function could also be given a nonlinear functional form as described in the apparent age or the product time functional behavior stored in the databases 110. However, visually realistic simulations of product behavior and de-aging are achieved using the linear relationship, which can be subsequently adjusted to exactly match visual changes in appearance due to products or age.

Figure 9:
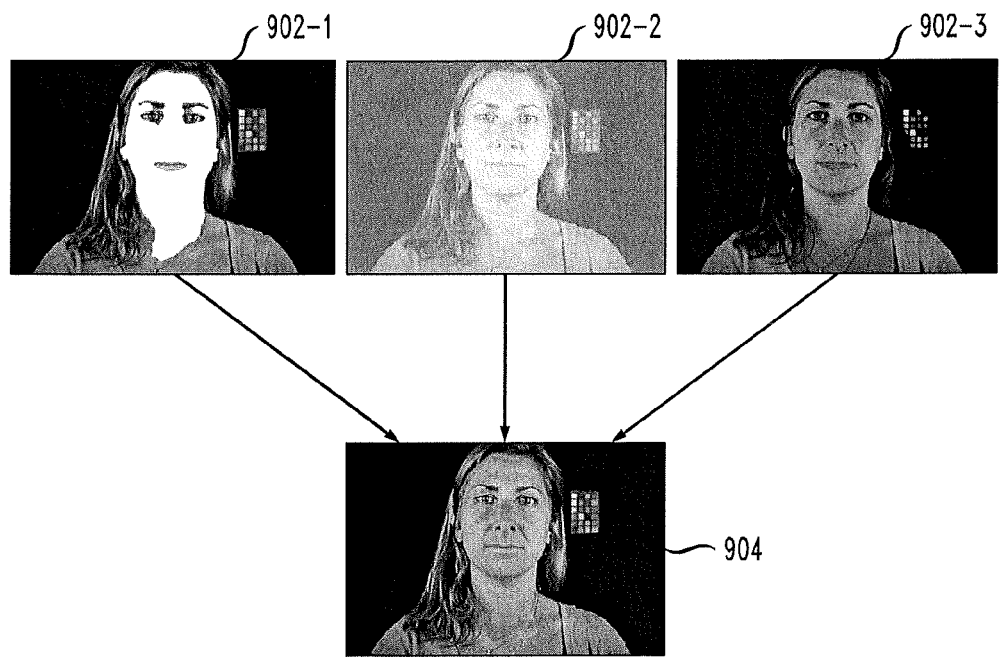
FIG. 9 illustrates an image compositing process of an image processing module of a skin diagnostic and image compositing system, according to one embodiment of the invention.
Figure 9:
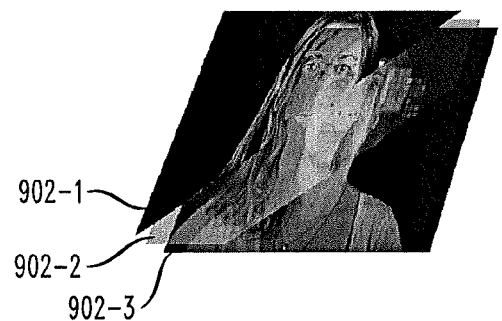

FIG. 9 illustrates an image compositing process, according to one embodiment of the invention. It is to be understood that the image compositing process in FIG. 9 is a visual example of the image component combining operations performed by image processing module 606 and described above in the context of FIG. 7.

As noted above, three image components are captured and processed as inputs, and a single image is created and displayed as the simulated user skin image. As depicted in FIG. 9, non-polarized image component 902-1 represents a structural template layer that serves as the proscenium for underlying layers. Parallel light image component 902-2 represents a parallel layer that is treated as described above based on pixel bender filters (for example, 50% opacity as provided by filter 710 in FIG. 7). Further, perpendicular light image component 902-3 represents a perpendicular layer that is treated as described above based on pixel bender filters (for example, 100% opacity as provided by filter 712 in FIG. 7).

Combined simulated user skin image 904 represents all three layers (902-1, 902-2, and 902-3) composited to form the final image. Further, by way of illustration, the bottom image in FIG. 9 represents the three layers (902-1, 902-2, and 902-3) in a 2.5-dimensional view.

As detailed above in the context of FIG. 7, image component 902-1 is generated by passing the non-polarized image component 702 through filter 708, which determines regions of skin in the image and these pixel regions are made transparent, while all other pixel regions remain unchanged to create the proscenium. The image component 902-2 and image component 902-3 are generated by passing the parallel light image component 704 and the perpendicular light image component 706 through respective filters 710 and 712, whose properties are controlled by parameters determined by clinical product behavior at different timepoints, as explained above. Thus, as represented in FIG. 9, the parallel image component and perpendicular image component are combined to form a non-polarized product behavior image for the subject or user, which is combined with the proscenium to form the displayed image. Additionally, in at least one embodiment of the invention, for single images captured, for example, with a mobile device (e.g., cell phone or tablet), the captured image is copied into non-polarized, parallel, and perpendicular inputs of the system, and the techniques subsequently proceed as detailed above.

Figure 10:
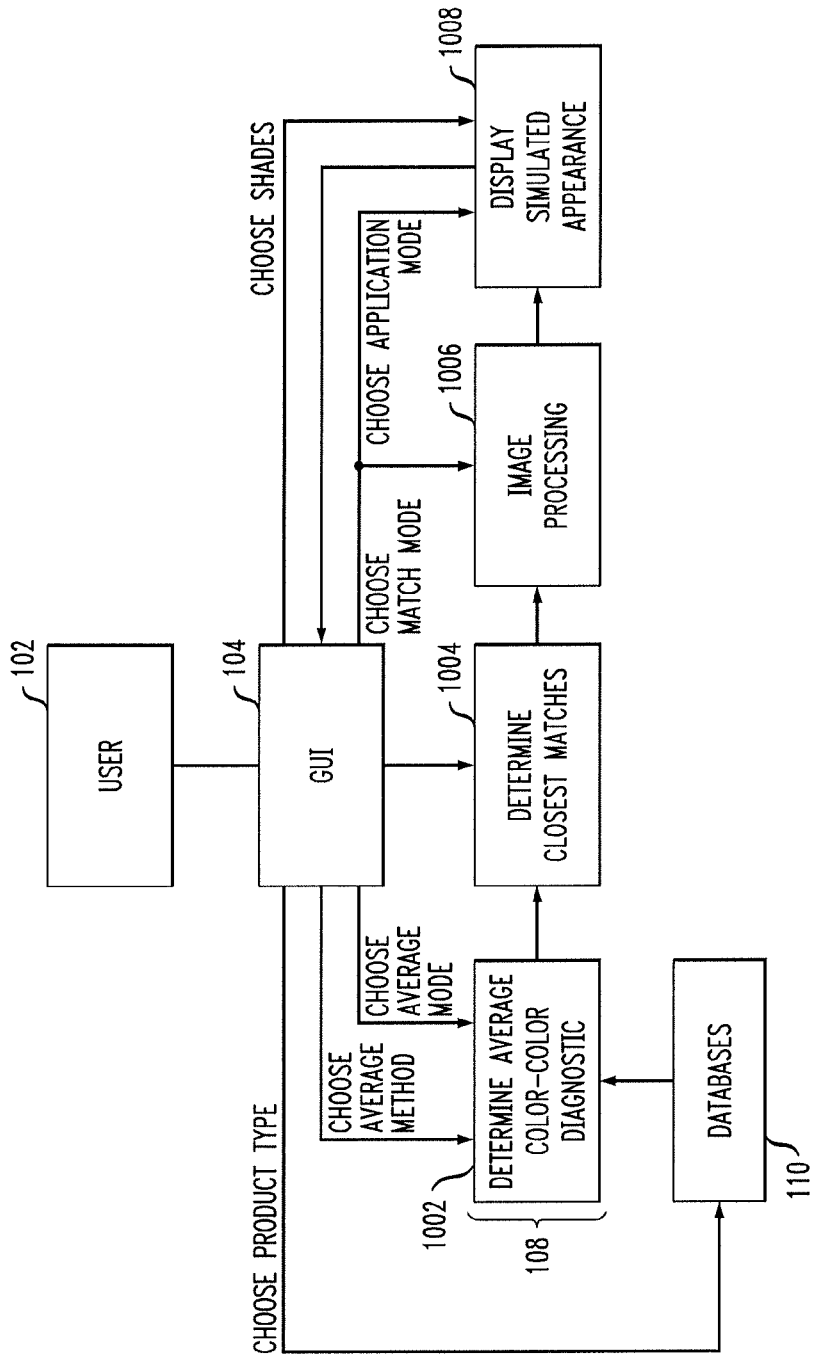
FIG. 10 illustrates an application module executing a foundation matching sub-application of a skin diagnostic and image compositing system, according to one embodiment of the invention.

FIG. 10 illustrates an application module 108 executing a foundation matching sub-application in accordance with the skin diagnostic and image compositing system 100 of FIG. 1. That is, it is assumed that the sub-application chosen in accordance with the selection module 604 from the plurality of sub-applications 612 through 620 (FIG. 6B) is foundation match sub-application 612. More particularly, modules 1002 through 1008 represent steps performed by the application module 108 of the system of FIG. 1.

It is assumed that at least one user skin image is obtained. Via the GUI 104, the user 102 chooses a product type and also selects an area in the user skin image that he/she wishes to have diagnosed or otherwise processed by the system, referred to as "choose average method" (FIG. 10). Simultaneously, data associated with the user's choice from the product type selection chosen (in this example, a foundation skincare product) is retrieved from the databases 110 and input into module 1002. Data obtained and/or processed by module 1002 is passed to module 1004 which then determines the closest match as described below in the context of FIG. 6A. After the initial visualization, the user 102 (if he/she so wishes) can choose another location in the user skin image to visualize the product effects. This is referred to as "choose average mode" (FIG. 10) which is within the particular choosen product type sub-application and enables the sub-application to display the product visualization elsewhere on the face.

Thus, in this specific example, module 1002 obtains the user skin image and determines average color values for the given area of the image selected by the user, i.e., generates skin image data from the skin image. Module 1004 identifies one or more sets of skin image data in the databases 110 that match or correspond to the user skin image data generated by module 1002. Module 1006 processes the image to determine the appropriate image processing filters (e.g., 708, 710, and 712 in FIG. 7) based on the one or more sets of identified skin image data from the database. Module 1006 then applies the image processing filters to the selected area of the user skin image to generate a simulated user skin image. The simulated user skin image is displayed to the user via module 1008 and the GUI 104.

Additionally, in conjunction with module 1008, the user 102 (via GUI 104) may select a match mode ("choose match mode") and an application mode ("choose application mode"), as well as one or more particular shades or tones ("choose shades"), if applicable. The application mode allows a user to apply a specific shade onto the skin, adjust how much is applied and allows the user to see half of the face (or some other percentage) with the product on the face while the other half (or remaining percentage) is his/her original image. The choose shades option allows the user to choose other shades other than the natural match shade to account for consumer preferences. The application can show shades that are lighter, darker, more yellow, or more red, as compared to the natural shade, but that would still be appropriate for the user. The match mode selection allows for choosing parameters used by the sub-application to find the closest matches.

As described herein, it is to be understood that diagnostic operations of the sub-application include determining user RGB color space values for one or more areas of the selected or identified portion of the user skin image. Additionally, the sub-application includes calculating average RGB color space values of the user RGB color space values for the areas of the selected portion of the user skin image, and converting the average RGB color space values to user L, a, b color space values. Further, one or more sets of skin image data are identified in the database that correspond to the user skin image data via identifying one or more L, a, b color space values in the database that approximately match the user L, a, b color space values. The appropriate image processing filters are determined and/or set based on the one or more identified L, a, b color space values from the database. Further, as described herein, the sub-application includes accessing a look-up table (LUT) for identifying one or more L, a, b color space values from one or more spectral feature values.

Thus, advantageously in the foundation matching example shown in FIG. 10, the average color is sampled in the localized region of a user skin image and the deviation from an actual product color stored in a LUT (in databases 110) is calculated. A pre-determined number of closest matches are returned. In an example embodiment of the invention, low, medium or high opacity coverage (e.g., ranging from about 0.3 to about 0.8 opacity) may be selected. Further, different regions of the user image can be resampled, returning matches for the original region. As described herein, the image processing filters are set to match particular product behaviors obtained through clinical product testing.

More particularly, in one embodiment, the user touches and/or selects an area of the image (for example, a cheek portion of the face). RGB values are averaged over a region (for example, a 50×50 pixel region) in the selected or touched region of the image. $R_{avg}$, $G_{avg}$, $B_{avg}$ values are converted to $L_{avg}$, $A_{avg}$, $B_{avg}$ color space values using conventional color model conversion techniques, and the deviation of $L_{avg}$, $A_{avg}$, $B_{avg}$ values from product colors stored in the databases 110 is calculated using the expression $E=\sqrt{((L-L_{avg})^2+((A-A_{avg})^2((B-B_{avg})^2)}$. A pre-determined number (for example, five) of the closest matches from the databases are returned and the RGB values for the relevant shades are returned and used to set the appropriate filters for image processing, i.e., generate and apply the filters for the appropriate foundation shades.

Such techniques and such an example application are useful, for example, for simulating the application of powder foundations and can be adjusted to clinically determined behavior. Further, as with other applications, the foundation matching application enables the user to redefine the sampling region using a GUI selection feature.

While FIG. 10 illustrates a foundation matching application, it is to be understood that the system 100 can perform other diagnostic applications to determine information from a selected region of a user skin image to set the behaviors of one or more skincare products based on the information derived from the selected user skin image region.

By way of further example, a skin lightening application (i.e., sub-application 616 in FIG. 6B) includes displaying time-point product behavior of a whitening or lightening skincare product. The image processing filters are set to match particular product behaviors obtained through clinical product testing. Another example application includes a facial region recognition and masking application. Facial masking allows for displaying only modified regions of skin by realizing that the color of selected skin falls within a particular range of color. Accordingly, a thresholding pixel bender filter is used to mask images.

A lines and wrinkles application (i.e., sub-application 614) includes displaying timepoint product behavior of line and wrinkle-related skincare products. The image processing filters are set to match particular product behaviors obtained through clinical product testing. More specifically, in accordance with a lines and wrinkles application, an image is chosen from a database or library, or a user image is captured. The user touches and/or selects an area of the image (for example, a cheek portion of the face). A box (by way of example, a 3"×3" box) blur is applied to the parallel image within the relevant image processing filter and the result is combined with the original parallel image. The opacity of the blur image is controlled by a calibration matrix and can, in general, vary from approximately 0.1 opacity at early product usage times to approximately 0.6 opacity at subsequent product usage times.

Advantageously, with the given processing and filtering framework provided herein, one of ordinary skill in the art will realize many additional applications that can be implemented by the skin diagnostic and image compositing system in a straightforward manner. Other examples include, but are not limited to, a pore application, skin non-uniformity application, and dark under eye circles application.

Figure 11:
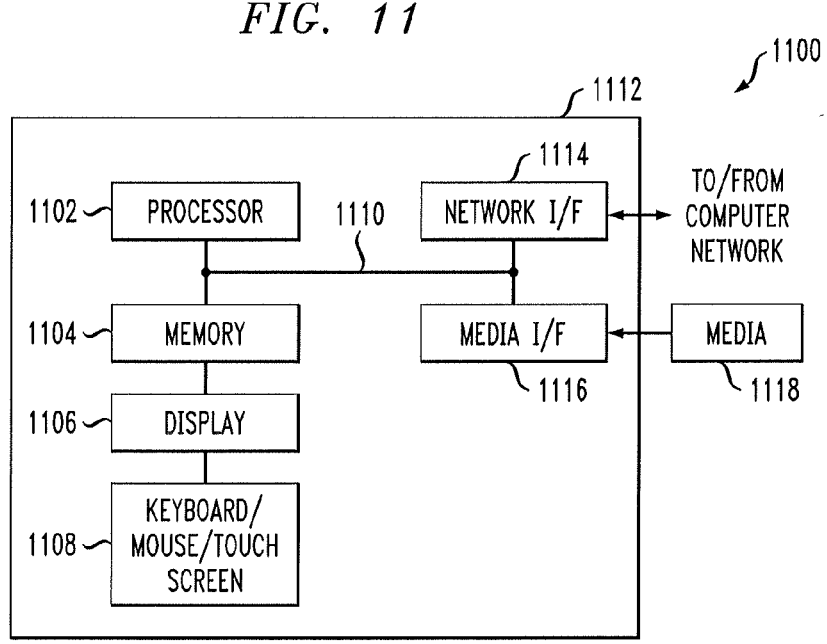
FIG. 11 illustrates a computer system in accordance with which one or more embodiments of the invention can be implemented.

FIG. 11 illustrates a computer system (processing platform) 1100 in accordance with which one or more embodiments of a skin diagnostic and image compositing system can be implemented. That is, one, more than one, or all of the components shown and described in the context of FIGS. 1-10 can be implemented via the processing platform depicted in FIG. 11.

By way of illustration, FIG. 11 depicts a processor 1102, a memory 1104, and an input/output (I/O) interface formed by a display 1106 and a keyboard/mouse/touchscreen 1108. More or less devices may be part of the I/O interface. The processor 1102, memory 1104 and I/O interface are interconnected via computer bus 1110 as part of a data processing unit or system 1112 (such as a general purpose computer, workstation, server, client device, etc.). Interconnections via computer bus 1110 are also provided to a network interface 1114 and a media interface 116. Network interface 1114 (which can include, for example, modems, routers and Ethernet cards) enables the system to couple to other data processing systems or devices (such as remote displays or other computing and storage devices) through intervening private or public computer networks (wired and/or wireless). Media interface 1116 (which can include, for example, a removable disk drive) interfaces with media 1118.

As used herein, the term "processor" refers to one or more individual processing devices including, for example, a central processing unit (CPU), a microprocessor, a microcontroller, an application-specific integrated circuit (ASIC), a field programmable gate array (FPGA) or other type of processing circuitry, as well as portions or combinations of such circuitry elements.

Additionally, the term "memory" refers to memory associated with a processor, such as, for example, random access memory (RAM), read only memory (ROM), a removable memory device, a fixed memory device, and/or a flash memory. Media 1118 may be an example of removable memory, while the other types of memory mentioned may be examples of memory 1104. Furthermore, the terms "memory" and "media" may be viewed as examples of what are more generally referred to as a "computer program product." A computer program product is configured to store computer program code (i.e., software, microcode, program instructions, etc.). For example, computer program code when loaded from memory 1104 and/or media 118 and executed by processor 1102 causes the device to perform functions associated with one or more of the components and techniques of system 100. One skilled in the art would be readily able to implement such computer program code given the teachings provided herein. Similarly, the components and techniques described herein may be implemented via a computer program product that includes computer program code stored in a "computer readable storage medium." Other examples of computer program products embodying embodiments of the invention may include, for example, optical or magnetic disks. Further, computer program code may be downloaded from a network (e.g., through network interface 1114) and executed by the system.

Still further, the I/O interface formed by devices 1106 and 1108 is used for inputting data to the processor 1102 and for providing initial, intermediate and/or final results associated with the processor 1102.

Figure 12:
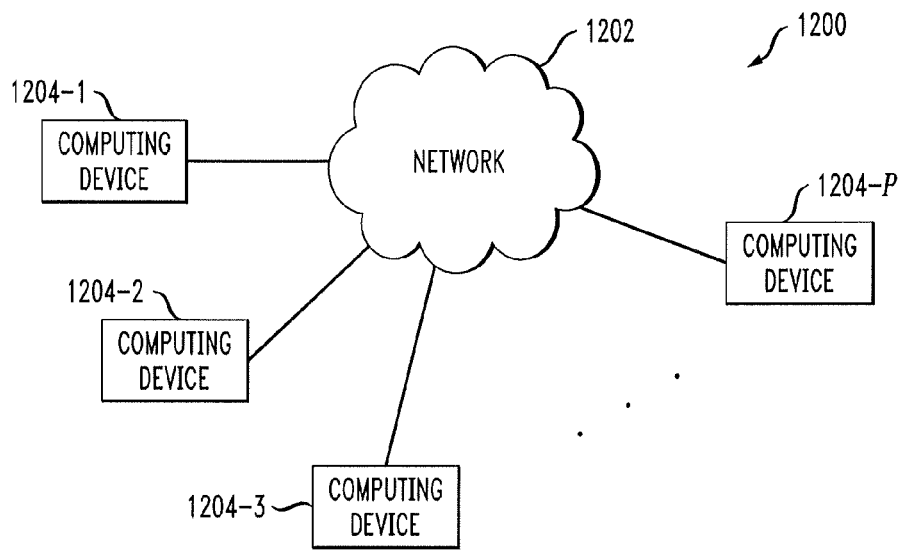
FIG. 12 illustrates a distributed communications/computing network in accordance with which one or more embodiments of the invention can be implemented.

FIG. 12 illustrates a distributed communications/computing network (processing platform) in accordance with which one or more embodiments of the invention can be implemented. By way of illustration, FIG. 12 depicts a communication system 1200 that includes a plurality of computing devices 1204-1 through 1204-P (herein collectively referred to as computing devices 1204) configured to communicate with one another over a network 1202.

It is to be appreciated that one, more than one, or all of the computing devices 1204 in FIG. 12 may be configured as shown in FIG. 11. The network 1202 may include, for example, a global computer network such as the Internet, a wide area network (WAN), a local area network (LAN), a satellite network, a telephone or cable network, or various portions or combinations of these and other types of networks (including wired and/or wireless networks).

As described herein, the computing devices 1204 may represent a large variety of devices. For example, the computing devices 1204 can include a portable device such as a mobile telephone, a smart phone, personal digital assistant (PDA), tablet, computer, a client device, etc. The computing devices 1204 may alternatively include a desktop or laptop personal computer (PC), a server, a microcomputer, a workstation, a kiosk, a mainframe computer, or any other information processing device which can implement any or all of the techniques detailed in accordance with one or more embodiments of the invention.

One or more of the computing devices 1204 may also be considered a "user." The term "user," as used in this context, should be understood to encompass, by way of example and without limitation, a user device, a person utilizing or otherwise associated with the device, or a combination of both. An operation described herein as being performed by a user may therefore, for example, be performed by a user device, a person utilizing or otherwise associated with the device, or by a combination of both the person and the device, the context of which is apparent from the description.

Additionally, as noted herein, one or more modules, elements or components described in connection with embodiments of the invention can be located geographically-remote from one or more other modules, elements or components. That is, for example, the modules, elements or components shown and described in the context of FIGS. 1 through 10 can be distributed in an Internet-based environment, a mobile telephony-based environment, a kiosk-based environment and/or a local area network environment. The skin diagnostic and image compositing system, as described herein, is not limited to any particular one of these implementation environments. However, depending on the diagnostic operations being performed by the system, one implementation environment may have some functional and/or physical benefits over another implementation environment.

By way of example, in an Internet-based and/or telephony-based environment, the system is configured to enable a user to capture (or select) an image via a smart phone or mobile device (one of the computing devices 1204 in FIG. 12), and the image is transmitted to a remote server (another one of the computing devices 1204 in FIG. 12) for processing and analysis such as detailed herein. At least a portion of the processing and analysis may be performed at the user end.

Additionally, for example, in a kiosk-based environment, a device (one of the computing devices 1204 in FIG. 12) captures an image or enables a user to select an image, and the image is transmitted through either a wired or wireless connection to a server (another one of the computing devices 1204 in FIG. 12) for processing and analysis as described herein. Again, at least a portion of the processing and analysis may be performed at the user end. The kiosk environment may be configured as described above in the context of FIG. 4.

In a LAN-based environment, all image capture, processing and analysis can be performed by one or more computing devices (1204 in FIG. 12) that are locally coupled to the LAN.

It is to be appreciated that combinations of the different implementation environments are contemplated as being within the scope of embodiments of the invention. One of ordinary skill in the art will realize alternative implementations given the illustrative teachings provided herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. Additionally, the terms "comprises" and/or "comprising," as used herein, specify the presence of stated values, features, steps, operations, modules, elements, and/or components, but do not preclude the presence or addition of another value, feature, step, operation, module, element, component, and/or group thereof.

The descriptions of the various embodiments of the invention have been presented for purposes of illustration, but are not intended to be exhaustive or limited to the embodiments disclosed. Many modifications and variations will be apparent to those of ordinary skill in the art without departing from the scope and spirit of the described embodiments.

What is claimed is:

1. A method comprising steps of:
   performing one or more diagnostic operations on at least one portion of a user skin image to generate user skin image data, wherein the one or more diagnostic operations are associated with an identified skin-related application;
   processing the user skin image data in accordance with the identified skin-related application, wherein said processing comprises:
   identifying one or more sets of skin image data in a database that correspond to the user skin image data based on one or more parameters specified by the skin-related application; and
   determining at least one image processing filter based on the one or more sets of identified skin image data from the database; and
   applying the at least one image processing filter to the at least one portion of the user skin image to generate a simulated user skin image;
   wherein the user skin image comprises a parallel light image component and a perpendicular light image component, and the step of applying the at least one image processing filter to the at least one portion of the user skin image further comprises determining component contribution amounts for one or more of the parallel image light component and the perpendicular image light component based on at least a portion of the identified skin image data;

wherein one or more of the above steps are carried out by at least one computing device comprising a processor and a memory configured to implement the at least one image processing filter; and wherein the parallel light image component comprises a specular component and first portion of an undertone component, and the perpendicular light image component comprises a second portion of the undertone component.

2. The method of claim 1, further comprising capturing a user skin image.

3. The method of claim 2, wherein capturing a user skin image further comprises capturing at least one visible image of a portion of skin of the user.

4. The method of claim 2, wherein capturing a user skin image further comprises capturing at least one infrared image of a portion of skin of the user.

5. The method of claim 2, wherein capturing a user skin image further comprises capturing at least one ultraviolet image of a portion of skin of the user.

6. The method of claim 2, further comprising providing the captured user skin image as a non-polarized image component, a parallel light image component and a perpendicular light image component.

7. The method of claim 1, further comprising capturing user information via a text capture device.

8. The method of claim 1, further comprising enabling selection of the skin-related application from a plurality of skin-related applications.

9. The method of claim 1, wherein performing one or more diagnostic operations further comprises determining user red, green, blue (RGB) color space values for one or more areas of the at least one portion of the user skin image.

10. The method of claim 9, further comprising calculating average RGB color space values of the user RGB color space values for the one or more areas of the at least one portion of the user skin image.

11. The method of claim 10, further comprising converting the average RGB color space values to user L, a, b color space values.

12. The method of claim 11, wherein identifying one or more sets of skin image data in the database that correspond to the user skin image data comprises identifying one or more L, a, b color space values in the database that approximately match the user L, a, b color space values.

13. The method of claim 12, wherein determining at least one image processing filter comprises setting the at least one image processing filter based on the one or more identified L, a, b color space values from the database.

14. The method of claim 12, further comprising accessing a look-up table for identifying one or more L, a, b color space values from one or more spectral feature values.

15. The method of claim 1, wherein the user skin image further comprises a non-polarized image component.

16. The method of claim 15, wherein determining at least one image processing filter based on the one or more sets of identified skin image data from the database comprises determining a non-polarized image filter, a parallel light image filter and a perpendicular light image filter.

17. The method of claim 16, wherein applying the at least one image processing filter to the at least one portion of the user skin image to generate a simulated user skin image further comprises:

applying the non-polarized image filter to the non-polarized image component to generate a proscenium image component;

applying the parallel light image filter to the parallel light image component to generate a simulated parallel light image component; and applying the perpendicular light image filter to the perpendicular light image component to generate a simulated perpendicular light image component.

18. The method of claim 17, further comprising combining the simulated parallel light image component and the simulated perpendicular light image component to generate a base simulated user image for the skin-related application.

19. The method of claim 18, further comprising combining the base simulated user image with the proscenium image component to generate the simulated user skin image.

20. The method of claim 1, further comprising outputting the simulated user skin image to a display.

21. The method of claim 1, further comprising enabling selection of the at least one portion of a user skin image via manipulation of a graphical user interface.

22. The method of claim 21, wherein manipulation of the graphical user interface comprises executing a before/after swiper tool across the user skin image.

23. The method of claim 21, wherein manipulation of the graphical user interface comprises executing a contrast operation on the user skin image.

24. The method of claim 21, wherein manipulation of the graphical user interface comprises executing a lighting simulation operation on the user skin image.

25. The method of claim 21, wherein manipulation of the graphical user interface comprises shrinking or enlarging the at least one portion of the user skin image via a sizing feature on the graphical user interface.

26. The method of claim 1, wherein the skin-related application comprises one of a foundation matching application, a lines and wrinkles application, a skin lightening application, a skin de-yellowing application, and a de-aging application.

27. The method of claim 1, wherein the skin-related application is identified via specification of at least one of a skin product and a skin product category.

28. The method of claim 1, wherein the one or more parameters specified by the skin-related application comprises a user demographic parameter.

29. The method of claim 1, wherein the one or more parameters specified by the skin-related application comprises a severity-time parameter.

30. A method comprising steps of:

obtaining a user skin image; and applying a set of image processing filters to polarized components associated with at least a portion of the user skin image to modify the user skin image, wherein the set of image processing filters is controlled by data identified based on a diagnosis of a skin condition from at least a portion of the user skin image, and wherein the identified data represents a previously-determined effect over time of a skincare product usage such that the modification to the user skin image visually simulates the subsequent effect over time of the skincare product usage;

wherein the polarized components associated with the user skin image comprise a parallel light image component and a perpendicular light image component, and modifying the user skin image to visually simulate the subsequent effect over time of the skincare product usage further comprises determining component contribution amounts for one or more of the parallel image light component and the perpendicular image light component based on at least a portion of the identified data;

wherein one or more of the above steps are carried out by at least one computing device comprising a processor and a memory configured to implement the set of image processing filters; and wherein the parallel light image component comprises a specular component and first portion of an undertone component, and the perpendicular light image component comprises a second portion of the undertone component.

31. The method of claim 30, further comprising presenting the modified user skin image to a user from whom the user skin image is obtained.

32. The method of claim 30, further comprising generating a sequence of images representing the modification of the user skin image over a plurality of sequential timepoints, and presenting the sequence of images to a user from whom the user skin image is obtained.

33. The method of claim 30, wherein the first portion of the undertone component and the second portion of the undertone component each represent half of the undertone component.

34. The method of claim 30, wherein modification of the user skin image further comprises adjusting over time, based on at least a portion of the identified data, one or more of the parallel light image component and the perpendicular light image component associated with the user skin image.

35. The method of claim 34, wherein one or more of the parallel light image component and the perpendicular light image component associated with the user skin image are adjusted as a function of an amount of change at one or more timepoints given by the identified data.

36. The method of claim 35, wherein the perpendicular light image component is adjusted by the change given in the identified data, and the parallel light image component is adjusted by a fraction of the change given in the identified data.

37. The method of claim 36, wherein the change given by the identified data represents a percentage change in melanin over time.

38. The method of claim 30, wherein the diagnosis of the skin condition is associated with a skin-related application comprising one of a foundation matching application, a lines and wrinkles application, a skin lightening application, a skin de-yellowing application, and a de-aging application.

* * * * *

UNITED STATES PATENT AND TRADEMARK OFFICE
CERTIFICATE OF CORRECTION

PATENT NO. : 9,101,320 B2
APPLICATION NO. : 13/859359
DATED : August 11, 2015
INVENTOR(S) : P. Cummins et al.

It is certified that error appears in the above-identified patent and that said Letters Patent is hereby corrected as shown below:

In the specification:

Column 8, line 38, please change "EXP^(0.012x * $MUA_{mel}\lambda$* (4.51 – $Log_{10}$(x * $MUA_{mel}$%)" to -- EXP^(0.012x * $MUA_{mel}\lambda$* (4.51 – $Log_{10}$(x * $MUA_{mel}\lambda$))) --

Column 8, line 40, please change "$MUA_{mei}$" to -- $MUA_{mel}$ --

Column 17, lines 31-32, please change "E=sqrt((L-$L_{avg}$)$^2$+((A–$A_{avg}$)$^2$((B–$B_{avg}$)$^2$)" to -- E=sqrt((L–$L_{avg}$)$^2$+((A–$A_{avg}$)$^2$ + (B–$B_{avg}$)$^2$)) --

Signed and Sealed this
Fifth Day of January, 2016

Michelle K. Lee
*Director of the United States Patent and Trademark Office*